United States Patent [19]

Tararine et al.

[11] Patent Number: 5,065,316
[45] Date of Patent: Nov. 12, 1991

[54] PROCESS FOR LOCATING NUCLEAR RADIATION WITH REDUCTION OF MOIRE PHENOMENON

[75] Inventors: Michel Tararine, Sceaux; Bernard Thevenin; Monique Marcaud, both of Saint Egreve, France

[73] Assignee: Commissariat A L'Energie Atomique, Paris, France

[21] Appl. No.: 198,400

[22] Filed: May 25, 1988

[30] Foreign Application Priority Data

May 27, 1987 [FR] France .................. 87 07481

[51] Int. Cl.$^5$ ................ G06F 15/42; G01T 1/202
[52] U.S. Cl. ..................... 364/413.24; 250/363.07
[58] Field of Search .......... 364/413.24; 250/363.07, 250/369

[56] References Cited

U.S. PATENT DOCUMENTS

| 3,745,345 | 7/1973 | Muehllenhner | 250/363.01 |
| 4,223,388 | 9/1980 | Nishikawa | 364/521 |
| 4,566,074 | 1/1986 | Nishikawa | 364/571.04 |
| 4,672,542 | 6/1987 | Roux et al. | 364/413.24 |
| 4,673,971 | 6/1987 | Ikuta et al. | 358/75 |
| 4,688,186 | 8/1987 | Ferrell et al. | 364/764 |
| 4,900,931 | 2/1990 | Tournier et al. | 250/369 |

FOREIGN PATENT DOCUMENTS 2387559 10/1978 France .

Primary Examiner—Dale M. Shaw
Assistant Examiner—David Huntley
Attorney, Agent, or Firm—Michael N. Meller

[57] ABSTRACT

The coordinates X and Y of the location of a scintillation crystal excited by nuclear radiation are determined as a function of the signals $X^+$, $X^-$, $Y^+$, $Y^-$ produced conventionally by an electronic circuit associated with the scintillation crystal. The signals $X^+$, $X^-$, $Y_+$ and $Y^-$ are digitized and the digital coordinate X (respectively Y) is obtained as the product of a first digital data item $X^+$-$X^-$ (respectively $Y^+$-$Y^-$) and a second digital data item inversely proportional to the energy of the nuclear radiation received. To prevent beats in the value of the coordinates X and Y, which leads to a moire phenomenon in the radiation image, a random element is introduced into the calculation, for example by adding p random bits to the first digital data item.

11 Claims, 1 Drawing Sheet

PROCESS FOR LOCATING NUCLEAR RADIATION WITH REDUCTION OF MOIRE PHENOMENON

BACKGROUND AND SUMMARY OF THE INVENTION

The present invention relates to a process for locating or localizing nuclear radiation. It is more particularly used in the medical field, where radiation image formation devices are used as a diagnosis aid. Such devices are generally referred to as a scintillation, gamma ray or ANGER camera. Such cameras are described in U.S. Pat. No. 3,011,057, U.S. Pat. No. 3,745,345 and FR-A-2 412 856.

The application of the invention to the medical field involves the administration by injection into a patient's vein of a small dose of a radioisotope (a radioactive substance emitting gamma rays). The blood flow distributes the dose within the body and a transducer having an appropriate sensitivity records the development of said distribution.

The regions of the body having a great affinity for the isotope or a rich blood irrigation appear as bright or highly illuminated sources, whereas conversely the low affinity or low blood irrigation regions appear dark. Thus, any part of the body or a specific organ can undergo a reliable surgery-free clinical investigation.

A gamma ray camera comprises a detection head generally constituted by a collimator for focussing the gamma rays emitted by the patient, a crystal for transforming the gamma photons into light photons or scintillations and a system of photomultiplier tubes for transforming each scintillation into an analog electric pulse, which is also called electrical contribution.

It also comprises a position coder for producing signals of coordinates X and Y of the place where a scintillation has occurred, on the basis of analog electric pulses supplied by the photomultiplier tubes.

Finally, a gamma ray camera generally comprises a cathode-ray oscilloscope controlled by signals for coordinates X and Y and by a validation signal Z produced by the position coder on the basis of pulses supplied by the photomultiplier tubes, when the scintillation energy belongs to a predetermined energy band. A gamma radiation reaching the crystal is thus rendered visible by a light spot on the cathode-ray oscilloscope screen.

In order to produce a radiation Image representative of all the nuclear radiations received, a gamma radiation camera can also have a photographic apparatus for forming an image of the organ observed by the accumulation of a large number of light spots produced on the cathode-ray oscilloscope screen, together with a digital processing means for the images, with a view to obtaining tomographs of the observed organ.

When a gamma radiation reaches the crystal, a scintillation is produced. It is known that such a scintillation is simultaneously seen by several, namely 6 to 10 photomultiplier tubes. The determination of the location of the scintillation is obtained by calculating the location of the barycenter of the electrical contributions supplied by all the photomultiplier tubes excited by said scintillation.

This calculation is performed in a conventional manner as described in U.S. Pat. No. 3,011,057, using several sets of electrical resistors, whereof the values are a function of the positions of the photomultiplier tubes to which they are connected. These positions are defined relative to a reference mark of axes Ox and Oy. In each set of resistors, there is one resistor per photomultiplier tube, each resistor being connected by one end to a photomultiplier tube and by another end to a common point. The signal supplied to this common point is consequently a weighting of the signals supplied by the photomultiplier tubes.

The position coder generally comprises 4 different sets of resistors, which supply analog signals designated $X+$, $X-$, $Y+$ and $Y-$. It can also comprise a fifth set of resistors for supplying the validation signal Z representing the scintillation energy.

According to the prior art, analog signals of coordinates X, Y are deduced, by an analog calculation, from signals $X+$, $X-$, $Y+$, $Y-$ and possibly the signal Z.

The relations generally used for calculating the coordinate X are one of the following:

$$X = \frac{X^+ - X^-}{X^+ + X^-} \text{ or}$$

$$X = \frac{X^+ - X^-}{X^+ + X^- + Y^+ + Y^-} \text{ or}$$

$$X = \frac{X^+ - X^-}{Z}$$

Symmetrical relations are used for calculating the coordinate Y.

The signals of coordinates X, Y obtained and, if applicable, the signal Z are then applied to the inputs of analog-digital converters for digitization. However, this method suffers from the disadvantage of requiring analog-digital converters with a very significant differential linearity.

French patent application 87 07482 entitled "Device for Locating Nuclear Radiation and Radiation Image Formation Device, incorporating such a Locating Device" filed in the name of the present inventor on the same date as the present application, proposes obviating this problem by digitizing the signals $X+$, $X-$, $Y+$, $Y-$ and then digitally calculating the coordinates X, Y by the aforementioned relations.

The relations defining the coordinates X, Y have a division operation. In practice, this calculation amounts to a multiplication operation between two operands, the first operand $O_1$ being $X+ - X-$ (for calculating the coordinate X) or $Y+ - Y-$ (for calculating the coordinate Y) and the second operand $O_2$ is inversely proportional to the energy D of the detected nuclear radiation. This energy D can be assumed as equal to one of the following values: $X+ + X-$, $X+ + X- + Y+ Y-$ or Z. The operand $O_2$ is of form K/D, in which K is a constant making it possible to have $O_2$ in integral form and which can be stored in a table, whereof the cell of address D contains K/D.

The number of bits $N_1$ of operand $O_1$ is a function of the possible accuracy of the digital data $X+$, $X-$, $Y+$, $Y-$. The accuracy is limited by the fact that the values of the electrical resistors used for producing the analog signals $X+$, $X-$, $Y+$, $Y-$ still have a certain dispersion with respect to their normal value. Therefore the maximum number of bits used for coding the operand $O_1$ is approximately 12 to 16 bits.

Preferably, operand $O_2$ is coded as a number of bits $n_2$ close to $n_1$. Data item D is coded as $n_1$ bits (or possibly $n_1+1$ bits), so that constant K must be coded over approximately $n_1+n_2$ bits.

Coordinates X and Y are obtained by multiplying together the operands $O_1$ and $O_2$. The result is coded as $n_1+n_2$ bits, i.e. at least 24 bits. Therefore, for a conventional scintillation crystal constituted by an approximately 400 mm diameter disk, all these bits are not significant. On e.g. only retaining 12 high-order bits, this gives a precision for the coordinates X and Y of 0.1 mm $(400/2^{12})$. Thus, in practice, coordinates X and Y are coded as m bits, in which $m < n_1+n_2$ by truncation of the bits with orders below $n_1+n_2-(m-1)$ of the product $O_1 \times O_2$.

The inventor has developed the process for determining coordinates X and Y described hereinbefore in a radiation image formation system. He has found that when a nuclear radiation uniformly excites the surface of the scintillation crystal, the system does not produce a uniform radiation image and instead produces an image having a significant moiré phenomenon, which is a major disadvantage which can prevent a correct interpretation of the radiation image produced by an analyzed organ.

The determination process for the coordinates X and Y described hereinbefore consequently reveals a new technical problem. The appearance of this moiré phenomenon is linked with the use of digital data and can be explained in the following way.

For a given application, use is made of a fixed energy nuclear radiation, e.g. the gamma photons produced by the radioactive isotopes $^{99}Te$ of technetium have an energy of 140 keV. Therefore the operand $O_2$, which is inversely proportional to the energy, has a fixed value.

It is known that the signals $X^+$, $X^-$ (respectively $Y^+, Y^-$) are linear functions of the coordinate X (respectively Y), so that the operand $O_1$, equal to $X^+ - X^-$ or $Y^+ - Y^-$ varies by a constant step P1 and the product $O_1 \times O_2$ varies by a constant step equal to $P1 \cdot O_2$. Moreover, to measure the coordinates X and Y, the product $O_1 \times O_2$ is truncated by eliminating the bits of orders below $n_1+n_2-(m-1)$, which amounts to measuring the coordinates X, Y by steps of P2 equal to $2^{n_1+n_2-m}$.

The steps $P1 \cdot O_2$ and P2 in each case produce a periodicity in the range of values of the coordinate X and the same applies for the coordinate Y. If these steps are different, there is a beat, i.e. a periodicity, which is visually translated by a moiré phenomenon.

In practice, this phenomenon is attenuated somewhat, because the energy of the nuclear radiation is not fixed and instead is subject to a certain statistical fluctuation. Therefore the operand $O_2$ is not constant and instead varies around a mean value. Thus, the step $P1 \cdot O_2$ is also not constant.

The low-order words of coordinates X, Y, i.e. the $n_1+n_2-m$ low-order bits which disappear by truncation are then distributed in a random manner over an interval which is a function of the width of the energy window of the nuclear radiation. When this interval is sufficiently great, the low-order words of coordinates X, Y are distributed in a random manner over all its possible values. The beats are then distributed over a wider interval than the largest value of the coordinates X, Y and the beats are no longer visible.

The moiré phenomenon is also attenuated when the energy of the nuclear radiation is greater. Thus, the variation step P1 of the differences $X^+ - X^-$ and $Y^+ - Y^-$ is greater, which reduces the spatial frequency of the beats. In practice, the statistical fluctuation of the energy of the nuclear radiation and the energy of the nuclear radiation itself are not adequate for completely masking the moiré phenomenon.

The invention aims at eliminating the moiré phenomenon, whose appearance is linked with the digital calculation of the coordinates X, Y from the digital data $X^+$, $X^-$, $Y^+$ and $Y^-$.

The invention consists of eliminating the beats by introducing a random element into the calculation of the coordinates X, Y.

According to a first embodiment, the operand $O_1$ is constituted by the digital data item $X^+ - X^-$ (or $Y^+ - Y^-$) completed to the right by p random bits ($p \geq 1$).

According to a second embodiment, 1 is added in random manner to the coordinate X, Y obtained after truncation.

More specifically, the present invention relates to a process for locating a nuclear radiation detected by a detection head incorporating a crystal for producing light photons in response to a received nuclear radiation and a group of transducers, each of which supplies an electric signal in response to the emitted light photons, said electric signals being combined to produce pairs of digital data $(X^+, X^-)$ and $(Y^+, Y^-)$, which are respectively a function of the coordinates X, Y of the location of the crystal excited by said nuclear radiation, said process consisting of digitally calculating the said coordinates X, Y expressed as m bits, as a function of said digital data expressed as n bits, said process being characterized in that:

a digital data item A, expressed as N bits and inversely proportional to the energy of the received nuclear radiation is determined, a digital data item B is determined by differentiation of the data of a pair of digital data items, a digital data item C is produced by completing B to the right by p bits ($p \geq 1$) of random values and the digital data items A and C are multiplied to produce a digital data item expressed as $N+n+p$ bits and the m high-power bits of said digital data item are retained, said m bits being the value of the coordinate X (respectively Y) when B is equal to $X^+ - X^-$ (respectively $Y^+ - Y^-$).

According to the second embodiment, the process is characterized in that a digital data item A, expressed as N bits and inversely proportional to the energy of the received nuclear radiation, is determined, a digital data item B is determined by differentiation of the data of a pair of digital data items, the digital data items A and B are multiplied to produce a digital data item expressed as $N+n$ bits and a digital data item F equal to the m high-order bits of said digital data item is produced and 1 is added in random manner to said data item F, the result being the value of the coordinate X (respectively Y) when B is equal to $X^+ - X^-$ (respectively $Y^+ - Y^-$).

The characteristics and advantages of the invention can be better gathered from the following description given in an illustrative, but non-limitative manner with reference to the attached drawings wherein:

DETAILED DESCRIPTION OF THE INVENTION

The invention relates to the location of a nuclear radiation and is particularly applicable to radiation image formation devices as described in the aforementioned U.S. Pat. No. 3,011,057, U.S. Pat. No. 3,745,345 and FR-A-241856.

More specifically, the invention relates to the digital calculation of the coordinates X, Y of the excitation location of a crystal forming part of a detection head of a radiation image formation device, on the basis of data $X^+$, $Y^-$, $Y^+$, $Y^-$ in digital form.

The inventive process can be advantageously realized by the digital calculating means or computer of the position coder described in the aforementioned French patent application entitled "Device for Locating Nuclear Radiation and Radiation Image Formation Device incorporating such a Locating Device".

The determination of the coordinates X, Y takes place in conventional manner on the basis of the signals $X^+$, $X^-$, $Y^+$, $Y^-$, which represent weighted sums of the signals supplied by transducers of the photomultiplier tube type included in a radiation image formation device. In the aforementioned French patent application, the Applicant has proposed coding these signals in the form of digital data.

Figure 1:
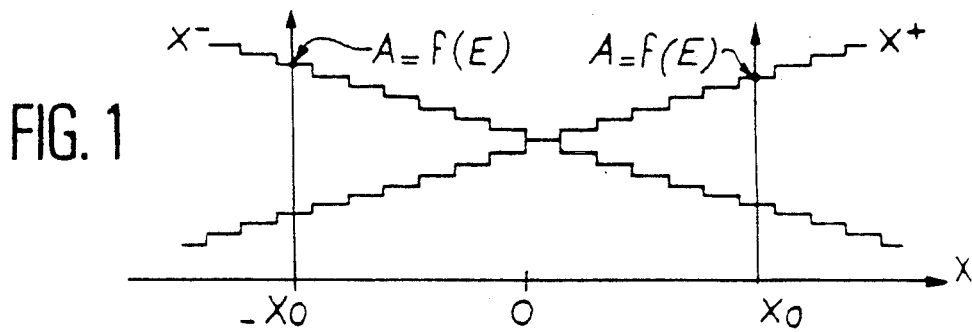
FIG. 1 shows the variation of the digital data $X^+$ and $X^-$ with the value of the coordinate X and the energy E.

The variation of the data $X^+$, $X^-$ is represented in FIG. 1. These data vary by constant steps as a function of the coordinate X and the energy E. The data $X^+$, $X^-$ are positive on the interval $[-X_0, X_0]$, which represents the amplitude range of X (point 0 being at the center of the image).

FIG. 1 shows that the difference $X^+ - X^-$ can be coded using the same number of bits n as the data $X^+$ and $X^-$ with the addition of one sign bit. It is also established that $X^+ + X^-$ is constant, but this is in reality only an approximation because the slope of signals $X^+$, $X^-$ varies with the energy of the nuclear radiation.

Figure 2:
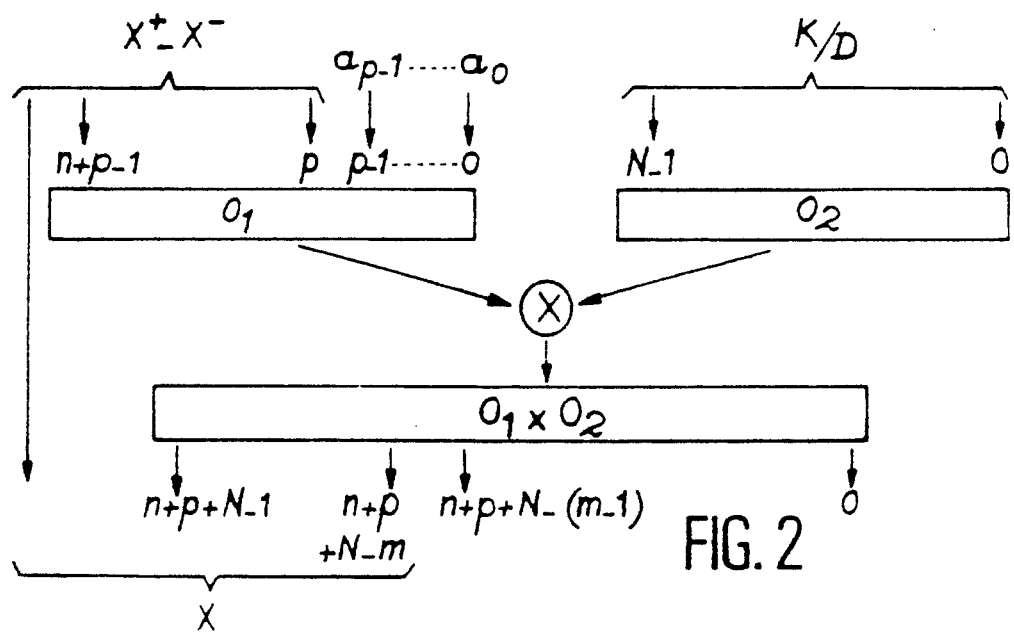
FIG. 2 depicts the process of the invention according to a first embodiment.

FIG. 2 diagrammatically illustrates a first embodiment of the inventive process. Coordinate X is calculated as a function of the product of a digital data item A equal to the difference $X^+ - X^-$ and a digital data item B, inversely proportional to the energy of the received nuclear radiation. The digital data item B is of form K/D, in which D can be equal in known manner to $X^+ + X^-$, $X^+ + X^- + Y^+ + Y^-$ or Z and where K is a constant chosen so that the ratio K/D is an integer.

According to the invention, a first operand $O_1$ is produced by completing the data item $X^+ - X^-$ by p bits $a_{p-1}, \ldots, a_0$, which values are determined in a random manner. The number of random bits p is at most a few units. A second operand $O_2$ is also produced by calculating D in accordance with one of the aforementioned relations and then by determining K/D, e.g. by having access to a table stored in a memory, which has a plurality of storage cells and whereof the storage cell of address D contains K/D.

The two operands $O_1$ and $O_2$ are e.g. expressed by 16 bits with n=12, p=4 and N=16.

The products are e.g. obtained by means of a 2×16 bit multiplier. For example, it is possible to use the AMD 29516 multiplier or any other commercially available multiplier.

Coordinate X is defined by the product $O_1 \times O_2$. The number of m high-order bits retained fixes the resolution on the coordinate axis. For a scintillation crystal with a radius of 20 cm, the resolution at X is 0.1 mm with m=11. The sign of the coordinate X is determined by a supplementary sign bit, which is the sign bit of the difference $X^+ - X^-$.

The obtaining of p random bits is brought about in conventional manner, for example, by using a counter permanently operated by a clock and making "copies" at each output event of the counter, the arrival time of the events being random.

This first embodiment of the invention has the advantage of being very easily performable.

Figure 3:
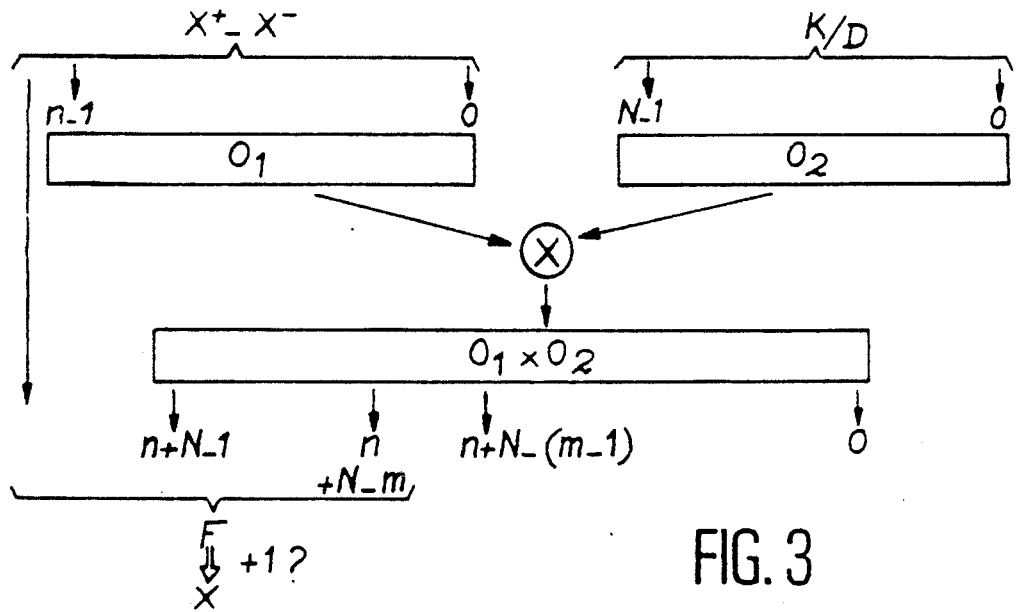
FIG. 3 depicts the process of the invention according to a second embodiment.

FIG. 3 illustrates another embodiment of the inventive process. Coordinate X is calculated as a function of the product of the same digital data items A and B as in the preceding embodiment. A first difference is that data item A is not completed and operands $O_1$ and $O_2$ are respectively equal to $X^+ - X^-$ and K/D.

Coordinate X is defined by the product $O_1 \times O_2$. As in the first embodiment, only an adequate number of m high-order bits are retained in order to obtain the desired resolution. To this digital data item F, expressed by m bits, is added at random times the value 1. The result constitutes the coordinate X. The random addition of the value 1 can e.g. be performed with a probability which is e.g. proportional to the value of bits with orders equal to or below $n+N-(m-1)$ of the product $O_1 \times O_2$.

This second embodiment makes it possible to cancel out the beats, whose periodicity is lower than the step P2 of the measurement of coordinate X, i.e. lower than $2^{n+N-m}$. Conversely, the beats with a periodicity higher than this do not disappear.

FIGS. 1 to 3 illustrate the determination of the coordinate X, coordinate Y being obtained in an identical manner.

The variations of the data items $Y^+$, $Y^-$ as a function of the coordinate Y are similar to the variations of the data items $X^+$, $X^-$ as a function of the coordinate X shown in FIG. 1. Coordinate Y is obtained as a function of the product of the data item A equal to $Y^+ - Y^-$ (instead of $X^+ - X^-$ for the coordinate X) and the data item B equal to K/D, in which D is generally chosen as equal to one of the following values: $Y^+ + Y^-$, $X^+ + X^- + Y^+ + Y^-$ or Z.

We claim:

1. A process for locating nuclear radiation detected by a detection head, said detection head incorporating a crystal and a group of transducers, comprising the following steps:

emitting light photons from said crystal in response to received nuclear radiation, supplying electrical signals from said transducers in response to emitted light photons, combining said electric signals to produce pairs of digital data $(X^+, X^-)$ and $(Y^+, Y^-)$, which are respectively a function of the coordinates X, Y of the location of the crystal excited by said nuclear radiation, and digitally calculating said coordinates X and Y expressed in m bits, as a function of said digital data expressed in n bits, said calculating step in turn comprising:

determining a digital data item A, expressed in N bits and inversely proportional to the energy of the received nuclear radiation, determining a digital data item B by performing a subtraction operation on a pair of digital data items, producing a digital data item C by completing the digital data item B to the right by p bits $a_{p-1}, \ldots, a_0$ (P>1) with random values, multiplying the digital data items A and C to produce a digital item Q expressed in N+n+p bits and retaining the m high-order bits or said digital data item, said m bits representing the value of the coordinate X (respectively Y) when B is chosen equal to $X^+ - X^-$ (respectively $Y^+ - Y^-$).

2. Process according to claim 1, wherein the digital data item A is of form K/D, in which K is a constant and D a digital data item proportional to the energy of the nuclear radiation received, said digital data item A being determined by reading in a table addressed by the digital data item D and containing the value K/D at address D.

3. Process according to claim 2, wherein D is chosen as equal to $X^+ + X^-$ (respectively $Y^+ + Y^-$) for calculating the coordinate X (respectively Y).

4. Process according to claim 2, wherein D is chosen as equal to $X^+ + X^- + Y^+ + Y^-$ for calculating the coordinates X, Y.

5. Process according to claim 2, wherein said electric signal supplied by said transducers are also combined to produce a digital data item Z, which is a function of the nuclear radiation energy received, and D is chosen equal to said digital data item Z.

6. A process for locating nuclear radiation detected by a detection head, said detection head incorporating a crystal and a group of transducers, comprising the following steps:

emitting light photons from said crystal in response to received nuclear radiation, supplying electrical signals from said transducers in response to emitted light photons, combining said electric signals to produce pairs of digital data items $(X^+, X^-)$ and $(Y^+, Y^-)$, which are respectively a function of the coordinates X,Y of the location of the crystal excited by said nuclear radiation, and digitally calculating said coordinates X, Y expressed in m bits, as a function of said digital data expressed in n bits, said calculating steps in turn comprising:

determining a digital data item A, expressed in N bits and inversely proportional to the energy of the received nuclear radiation, determining a digital data item B by performing a mathematical operation on a pair of said digital data items, multiplying the digital data items A and B to produce a digital data item R expressed in N+n bits, producing a digital data item F by retaining m high-order bits of said digital data item R, and adding the value 1 at random times to said digital data item F, the result representing the value of the coordinate X (respectively Y) on choosing B equal to $X^+ - X^-$ (respectively $Y^+ - Y^-$).

7. Process according to claim 6, wherein the value 1 is added to the digital data item F with a probability which is a function of the bits with an order equal to or below N+n−m of the product A×B expressed in N+n bits.

8. Process according to claim 6 wherein the digital data item A is of form K/D, in which K is a constant and D a digital data item proportional to the energy of the nuclear radiation received, said digital data item A being determined by reading in a table addressed by the digital data item D and containing the value K/D at address D.

9. Process according to claim 8, wherein D is chosen as equal to $X^+ + X^-$ (respectively $Y^+ + Y^-$) for calculating the coordinate X (respectively Y).

10. Process according to claim 8, wherein D is chosen as equal to $X^+ + X^- + Y^+ + Y^-$ for calculating coordinates X and Y.

11. Process according to claim 8, wherein said electric signals supplied by said transducers are also combined to produce a digital data item Z, which is a function of the energy of the nuclear radiation received, and D is chosen equal to said digital data item Z.

* * * * *